United States Patent
Zottola

(10) Patent No.: US 10,335,599 B2
(45) Date of Patent: *Jul. 2, 2019

(54) METHOD AND APPARATUS FOR PROGRAMMING CHARGE RECOVERY IN NEUROSTIMULATION WAVEFORM

(71) Applicant: Boston Scientific Neuromodulation Corporation, Valencia, CA (US)

(72) Inventor: Dennis Zottola, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 8 days.

This patent is subject to a terminal disclaimer.

(21) Appl. No.: 15/670,770

(22) Filed: Aug. 7, 2017

(65) Prior Publication Data
US 2017/0333717 A1    Nov. 23, 2017

Related U.S. Application Data

(63) Continuation of application No. 15/013,734, filed on Feb. 2, 2016, now Pat. No. 9,737,714.
(Continued)

(51) Int. Cl.
*A61N 1/36* (2006.01)
*A61N 1/372* (2006.01)

(52) U.S. Cl.
CPC ........... *A61N 1/36128* (2013.01); *A61N 1/36* (2013.01); *A61N 1/3605* (2013.01); *A61N 1/36146* (2013.01); *A61N 1/37247* (2013.01)

(58) Field of Classification Search
CPC ............ A61N 1/36128; A61N 1/36146; A61N 1/3605; A61N 1/36; A61N 1/37247
See application file for complete search history.

(56) References Cited

U.S. PATENT DOCUMENTS

| 7,783,353 | B2 | 8/2010 | Libbus et al. |
| 7,801,600 | B1 | 9/2010 | Carbunaru et al. |

(Continued)

FOREIGN PATENT DOCUMENTS

| AU | 2016215425 B2 | 7/2018 |
| CN | 107249681 A | 10/2017 |

(Continued)

OTHER PUBLICATIONS

"U.S. Appl. No. 15/013,734, Examiner Interview Summary dated Mar. 14, 2017", 3 pgs.
(Continued)

*Primary Examiner* — Catherine M Voorhees
(74) *Attorney, Agent, or Firm* — Schwegman Lundberg & Woessner, P.A.

(57) ABSTRACT

An example of a neurostimulation system may include a storage device to store a stimulation waveform, a programming control circuit to generate a plurality of stimulation parameters controlling delivery of neurostimulation pulses according to the stimulation waveform, and waveform definition circuit configured to create and adjust the stimulation waveform. The waveform definition circuit includes a charge recovery module that may include a stimulation to receive the stimulation waveform including charge injection phases, a charge recovery scheme input to receive a charge recovery scheme, and a waveform adjuster configured to identify a need for recovering charges injected during the charge injection phases and adjust the received stimulation waveform by automatically inserting charge recovery phases into the received stimulation waveform based on the identified need for recovering the injected charges and the received charge recovery scheme.

20 Claims, 7 Drawing Sheets

Related U.S. Application Data

(60) Provisional application No. 62/111,715, filed on Feb. 4, 2015.

(56) References Cited

U.S. PATENT DOCUMENTS

| | | | |
|---|---|---|---|
| 8,285,389 | B2 | 10/2012 | Libbus et al. |
| 8,874,211 | B2 | 10/2014 | Libbus et al. |
| 8,897,881 | B2 | 11/2014 | Libbus et al. |
| 9,265,948 | B2 | 2/2016 | Libbus et al. |
| 9,737,714 | B2* | 8/2017 | Zottola .............. A61N 1/36 |
| 9,737,717 | B2 | 8/2017 | Moffitt et al. |
| 9,802,052 | B2* | 10/2017 | Marnfeldt .......... A61N 1/36167 |
| 2003/0236558 | A1 | 12/2003 | Whitehurst et al. |
| 2004/0181262 | A1 | 9/2004 | Bauhahn |
| 2010/0274320 | A1* | 10/2010 | Torgerson .......... A61N 1/37247 607/59 |
| 2011/0106214 | A1* | 5/2011 | Carbunaru ......... A61N 1/36128 607/60 |
| 2012/0259384 | A1 | 10/2012 | Trier et al. |
| 2013/0310901 | A1 | 11/2013 | Perryman et al. |
| 2014/0243924 | A1 | 8/2014 | Zhu et al. |
| 2014/0243942 | A1 | 8/2014 | Zhu et al. |
| 2014/0257428 | A1* | 9/2014 | Zhu .................. A61N 1/36178 607/46 |
| 2016/0121126 | A1 | 5/2016 | Marnfeldt |
| 2016/0220820 | A1 | 8/2016 | Zottola |

FOREIGN PATENT DOCUMENTS

| | | |
|---|---|---|
| JP | 09512744 A | 12/1997 |
| JP | 2010501269 A | 1/2010 |
| JP | 2010536530 A | 12/2010 |
| JP | 2013031708 A | 2/2013 |
| JP | 2014012200 A | 1/2014 |
| JP | 2014524279 A | 9/2014 |
| JP | 2014533525 A | 12/2014 |
| JP | 2018504237 A | 2/2018 |
| WO | WO-2016126718 A1 | 8/2016 |

OTHER PUBLICATIONS

"U.S. Appl. No. 15/013,734, Examiner Interview Summary dated Jul. 18, 2017", 2 pgs.

"U.S. Appl. No. 15/013,734, Non Final Office Action dated Dec. 30, 2016", 14 pgs.

"U.S. Appl. No. 15/013,734, Notice of Allowance dated Apr. 19, 2017", 8 pgs.

"U.S. Appl. No. 15/013,734, Response filed Mar. 14, 2017 to Non Final Office Action dated Dec. 30, 2016", 15 pgs.

"International Application Serial No. PCT/US2016/016190, International Search Report dated Apr. 21, 2016", 5 pgs.

"International Application Serial No. PCT/US2016/016190, Written Opinion dated Apr. 21, 2016", 6 pgs.

"Australian Application Serial No. 2016215425, First Examiners Report dated Nov. 2, 2017", 4 pgs.

"Australian Application Serial No. 2016215425, Response filed Feb. 14, 2018 to First Examiners Report dated Nov. 2, 2017", 16 pgs.

"European Application Serial No. 16704354.6, Response filed May 7, 2018 to Communcation Pursuant to Rules 161 and 162 dated Oct. 27, 2017", 13 pgs.

"International Application Serial No. PCT/US2016/016190, International Preliminary Report on Patentability dated Aug. 17, 2017", 8 pgs.

"Japanese Application Serial No. 2017-541307, Office Action dated Aug. 6, 2018", w/ English translation, 2 pgs.

"Japanese Application Serial No. 2017-541307, Response filed Nov. 5, 2018 to Office Action dated Aug. 6, 2018", w/ English claims, 9 pgs.

* cited by examiner

METHOD AND APPARATUS FOR PROGRAMMING CHARGE RECOVERY IN NEUROSTIMULATION WAVEFORM

This application is a continuation of U.S. application Ser. No. 15/013,734, filed Feb. 2, 2016, which claims the benefit of priority under 35 U.S.C. § 119(e) of U.S. Provisional Patent Application Ser. No. 62/111,715, filed on Feb. 4, 2015, each of which is herein incorporated by reference in its entirety.

TECHNICAL FIELD

Technical Field

This document relates generally to neurostimulation and more particularly to a method and system for programming charge recovery in a stimulation waveform that represents a pattern of neurostimulation pulses.

Background

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. The patterns of neurostimulation pulses may each include charge injection and recovery pulses to ensure patient safety and/or longevity of electrodes used to deliver the pulses. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and waveform patterns predetermined at the time of manufacturing may substantially limit the potential for the customization. In various applications, the customization may require pulse-by-pulse programmability with recovery of charge injected with each pulse, thereby making the programming of the complete pulse pattern a challenging task.

SUMMARY

An example (e.g., "Example 1") of a neurostimulation system may include a storage device, a programming control circuit, and a waveform definition circuit. The storage device may store a stimulation waveform representing a pattern of neurostimulation pulses during a stimulation period. The programming control circuit may be configured to generate a plurality of stimulation parameters controlling delivery of the neurostimulation pulses according to the stimulation waveform. The waveform definition circuit is coupled to the storage device and the control circuit and may be configured to create and adjust the stimulation waveform. The waveform definition circuit includes a charge recovery module that may include a stimulation waveform input, a charge recovery scheme input, and a waveform adjuster. The stimulation waveform input may be configured to receive the stimulation waveform with each neurostimulation pulse in the pattern of the neurostimulation pulses including a charge injection phase. The charge recovery scheme input may be configured to receive a charge recovery scheme. The waveform adjuster may be configured to identify a need for recovering charges injected during the charge injection phases and adjust the received stimulation waveform by automatically inserting charge recovery phases into the received stimulation waveform based on the identified need for recovering the injected charges and the received charge recovery scheme.

In Example 2, the subject matter of Example 1 may optionally be configured such that the charge recovery scheme input is configured to display one or more parameters associated with the received charge recovery scheme and receive a value for each parameter of the displayed one or more parameters.

In Example 3, the subject matter of any one or a combination of Examples 1 and 2 may optionally be configured such that the charge recovery scheme input is configured to display one or more questions associated with the received charge recovery scheme and receive an answer for each questions of the displayed one or more questions.

In Example 4, the subject matter of any one or any combination of Examples 1-3 may optionally be configured such that the charge recovery scheme input is configured to display a plurality of predefined charge recovery schemes and receive the charge recovery scheme by receiving a selection from the displayed plurality of predefined charge recovery schemes.

In Example 5, the subject matter of any one or any combination of Examples 1-4 may optionally be configured such that the waveform adjuster is configured to adjust the received stimulation waveform by automatically adjusting existing charge recovery phases in the received stimulation waveform based on the identified need for recovering the injected charges and the plurality of charge recovery parameters.

In Example 6, the subject matter of any one or any combination of Examples 1-5 may optionally be configured such that the charge recovery module includes a charge recovery parameter generator configured to generate a plurality of charge recovery parameters based on the received charge recovery scheme and predetermined default values, and the waveform adjuster is configured to adjust the received stimulation waveform by automatically inserting the charge recovery phases into the received stimulation waveform based on the identified need for recovering the injected charges and the plurality of charge recovery parameters.

In Example 7, the subject matter of Example 6 may optionally be configured such that the charge recovery parameter generator is configured to generate the plurality of charge recovery parameters based on the received charge recovery scheme and one or more predetermined limiting values for one or more charge recovery parameters of the plurality of charge recovery parameters.

In Example 8, the subject matter of any one or any combination of Examples 1-7 may optionally be configured such that the waveform adjuster is configured to produce a warning message in response to the adjusted stimulation waveform not having an acceptable level of charge balance after the charge recovery phases are automatically inserted into the received stimulation waveform.

In Example 9, the subject matter of any one or any combination of Examples 1-8 may optionally be configured to include a graphical user interface (GUI) including the waveform definition circuit, the GUI configured to display the stimulation waveform, allow for entry of the charge recovery scheme, and allow for adjustment of the stimulation waveform.

In Example 10, the subject matter of Example 9 may optionally be configured such that the waveform adjuster is configured to allow adjustment of the stimulation waveform by graphically editing the stimulation waveform using the GUI.

In Example 11, the subject matter of any one or a combination of Examples 9 and 10 may optionally be configured to further include an implantable stimulation device and a programming device. The implantable stimulation device may include a stimulation output circuit configured to deliver the neurostimulation pulses and a stimulation control circuit configured to control the delivery of the neurostimulation pulses using the plurality of stimulation parameters. The programming device may be communicatively coupled to the stimulation device and include the storage device, the programming circuit, and the GUI.

An example (e.g., "Example 12") of a method for defining a waveform by a user may include receiving a stimulation waveform representing a pattern of neurostimulation pulses during a stimulation period. Each pulse in the pattern of the neurostimulation pulses includes a charge injection phase. The method further includes receiving a charge recovery scheme from the user, identifying a need for recovering charges injected during the charge injection phases, and adjusting the received stimulation waveform by automatically inserting charge recovery phases into the received stimulation waveform based on the identified need for recovering the injected charges and the received charge recovery scheme using a processing circuit of the programming device.

In Example 13, the subject matter of receiving the charge recovery scheme from the user as found in Example 12 may optionally include displaying a plurality of predefined charge recovery schemes and receiving a selection of a charge recovery scheme from the displayed plurality of predefined charge recovery schemes.

In Example 14, the subject matter of any one or a combination of Examples 12 and 13 may optionally further include displaying the adjusted stimulation waveform after the charge recovery phases are automatically inserted using a graphical user interface (GUI) and allowing the user to adjust the displayed stimulation waveform.

In Example 15, the subject matter of any one or any combination of Examples 12-14 may optionally further include indicating that an acceptable level of charge balance is not achieved based on the received stimulation waveform and the received charge recovery scheme.

In Example 16, the subject matter of any one or any combination of Examples 12-15 may optionally further include generating a plurality of stimulation parameters based on the stimulation waveform, the plurality of stimulation parameters allowing for delivery of the neurostimulation from a stimulation device to be controlled according to the stimulation waveform.

In Example 17, the subject matter of Example 16 may optionally further include transmitting the plurality of stimulation parameters to an implantable stimulator and controlling delivery of the neurostimulation pulses from the implantable stimulator using the plurality of stimulation parameters.

In Example 18, the subject matter of any one or any combination of Examples 12-17 may optionally include generating a plurality of charge recovery parameters based on the received charge recovery scheme and one or more predetermined values of each parameter of one or more stored parameters of the plurality of charge recovery parameters.

In Example 19, the one or more predetermined values of the each parameter of the one or more stored parameters as found in Example 18 may optionally include one or more limits each being a maximum or minimum value of the each parameter of the one or more stored parameters determined to ensure effective charge recovery.

In Example 20, the subject matter of any one or any combination of Examples 14-19 may optionally include allowing the user to graphically edit the automatically inserted charge recovery phases in the displayed stimulation waveform using the GUI.

In Example 21, the subject matter of any one or any combination of Examples 14-20 may optionally include allowing the user to graphically edit the charge injection phases in the displayed stimulation waveform using the GUI.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
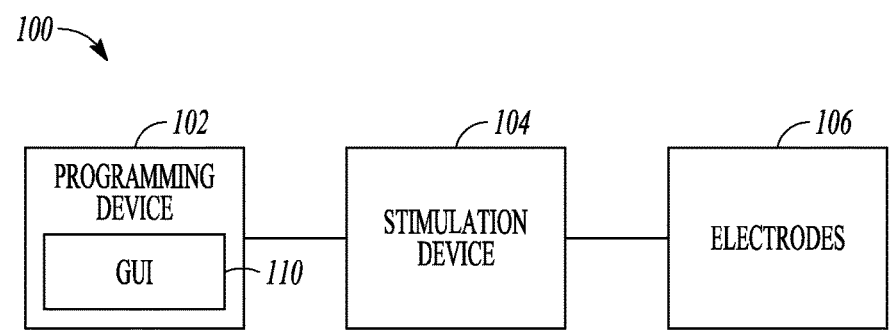
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for programming neurostimulation pulse patterns, including automatic definition of charge recovery phases. Advancements in neuroscience and neurostimulation research have led to a demand for using complex and/or individually optimized patterns of neurostimulation pulses for more and/or improved therapeutic effects. The capability of a neurostimulation system in treating various types of disorders will be limited by the programmability of such patterns of neurostimulation pulses. Because such a task may be performed at least in part by a user such as a physician or other caregiver with the patient in a clinical setting, there is a need for an intuitive, user-friendly, and efficient method and system for programming the neurostimulation pulse pattern.

A neurostimulation pulse may include a charge injection phase followed by a charge recovery phase. During the charge injection phase, charge is injected into targeted neural tissue to elicit an action potential through electrodes including at least one anode and one cathode. During the charge recovery phase, the anode and cathode are switched to recover the injected charge. Without recovering the injected charge, the neural tissue maybe harmed and/or the electrodes may suffer long term damage.

In a simple, tonic train of identical neurostimulation pulses, a charge recovery phase may immediately follow a charge injection pulse for each of the neurostimulation pulses. This may not be possible for a complex pattern of neurostimulation pulses. For example, following the charge injection phase of a neurostimulation pulse, there may not be sufficient time for completely recovering the injected charge before the charge injection phase of the next neurostimulation pulse is programmed to start. Thus, for a rapid burst of neurostimulation pulses, their charge injection phases may occur in sequence followed by one or more charge recovery phases to obtain charge balance. Examples of various patterns of charge injection and recovery phases are discussed in U.S. Patent Application Publication No. 2014/0243924 A1, entitled "NEUROSTIMULATION SYSTEM HAVING INCREASED FLEXIBILITY FOR CREATING COMPLEX PULSE TRAINS," filed on Feb. 21, 2014, assigned to Boston Scientific Neuromodulation Corporation, which is incorporated by reference in its entirety.

When defining a complex pattern of neurostimulation pulses, especially when it is impossible or impractical to have a charge recovery phase immediately following a charge injection phase for each and every pulse in the pattern, the requirement for considering charge recovery may become a substantially undesirable burden for the user. The present system allows the user who defines a complex pattern of neurostimulation pulses to focus on the charge injection phases without initially considering the charge recovery phases. In various embodiments, the system automatically adds the charge recovery phases to the complex pattern of neurostimulation pulses based on the charge injection phases that have been defined. The user may adjust the automatically arranged charge recovery phases if needed.

In various embodiments, the present system receives a complex pattern of neurostimulation pulses that may not include charge recovery phases and a charge recovery scheme specified by the user, and automatically inserts the charge recovery phases according to parameters of the charge recovery scheme. For example, the present system may allow the user to define the complex pattern of neurostimulation pulses including the charge rejection phases using a graphical user interface (GUI), and allows the user to set and/or adjust parameters of the charge recovery scheme in an intuitive way. The present system then automatically inserts the charge recovery phases into the complex pattern of neurostimulation pulses and displays the results on the GUI. The user is allowed to view various portions of the resulting waveform with the charge recovery phases and modify if necessary or desirable. If complete charge balance cannot be achieved reliably based on the complex pattern of neurostimulation and the user-specified charge recovery scheme, the present system may present a warn message to the user, such that the user may make necessary adjustments to the complex pattern of neurostimulation and/or the charge recovery scheme. In various embodiments, the present system may substantially reduce or eliminate the burden of considering charge recovery phases during the creation of a complex stimulation waveform and allow the user to focus on defining the charge injection phases of the complex stimulation waveform.

In this document, a "stimulation waveform" refers to the waveform representing a pattern of neurostimulation pulses. A "neurostimulation pulse" includes at least a "charge injection phase" (also known as a "stimulation phase", "stimulation pulse", or "cathodic phase") that is the portion of the neurostimulation pulse intended for eliciting an action potential in the target neural tissue. A "charge recovery phase" (also known as "recharge phase", "recharge pulse", or 'charge recovery pulse") is the portion of the neurostimulation pulse intended for recovering the charge injected into the target neural tissue during the charge injection phase. The recovery (or recharge) phase may also allow for preparation of charge injection in the next stimulation pulse, such as by recharging the capacitor in which the charge to be injected is stored.

In various embodiments, the present system facilitates creation and adjustment of complex patterns of neurostimulation pulses, such as a pattern that includes sequences of short bursts of pulses where the bursts and the pulses may each have different amplitude and timing parameters. In various embodiments, the present system enables fast and intuitive definition of patterns of neurostimulation pulses in a way that allows the patterns to be designed, tested, and modified in real time. While the application in neurostimulation is discussed as a specific example, the present subject matter allows for waveform definition with automatic or semi-automatic charge balancing in any electrical stimulation and other medical device applications in which a waveform representing a pattern or sequence of stimulation pulses is to be defined.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 includes a graphical user interface (GUI) 110 that allows the user to set and/or adjust values of the user-programmable parameters by creating and/or editing graphical representations of various waveforms. Such waveforms may include, for example, the waveform of a pattern of neurostimulation pulses to be delivered to the patient as well as individual waveforms that are used as building blocks of the pattern of neurostimulation pulses, such as the waveform of each pulse in the pattern of neurostimulation pulses. The user may also be allowed to define an electrode selection specific to each individually defined waveform. It is to be understood, however, that while GUI 110 provides the user with an intuitive and user-friendly means for programming various waveforms for neurostimulation, it is not necessary for the automatic definition of charge recovery phases according to the present subject matter.

Figure 2:
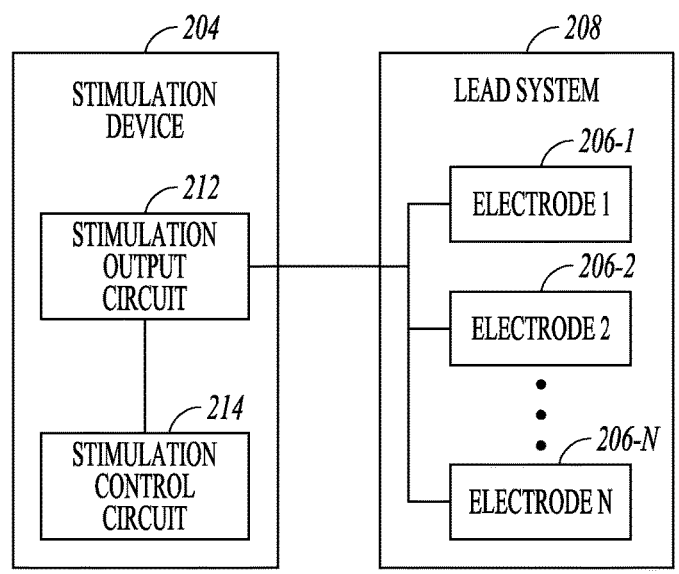
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

In various embodiments, charge balance is to be achieved for each set of electrodes selected from electrodes 206 for delivering one or more neurostimulation pulses. Charges injected into target tissue through the set of electrodes during the one or more neurostimulation pulses are balanced using one or more charge recovery phases, during which the anode(s) and cathode(s) of the same set of electrodes are switched. Thus, charge balance is achieved with one or more charge injection phases and one or more charge recovery phases associated with a common set of electrodes selected from electrodes 206.

Figure 3:
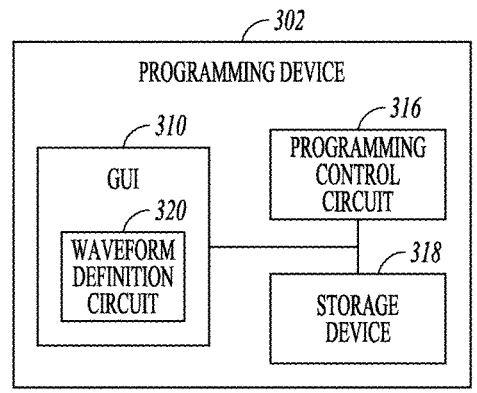
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a GUI 310. Storage device 318 stores a stimulation waveform representing a pattern of neurostimulation pulses during a stimulation period. Programming control circuit 316 generates the plurality of stimulation parameters that controls the delivery of the neurostimulation pulses according to the stimulation waveform. GUI 310 represents an embodiment of GUI 110 and includes a waveform definition circuit 320 that allows for definition of the pattern of neurostimulation pulses by creating and/or adjusting the stimulation waveform using a graphical method. In various embodiments, GUI 310 allows the user to define the stimulation waveform including at least the charge injection phase for each pulse of the neurostimulation pulses, with or without a corresponding charge recovery phase, and automatically adjust the stimulation waveform to add or rearrange the corresponding charge recovery phase. Waveform definition circuit 320 is configured to present the stimulation waveform using the GUI and allow user to adjust the stimulation waveform using graphical or other means of editing. It is to be understood that while the GUI is specifically discussed by way of example for implementing the automatic definition of charge recovery phases, the present subject matter can be implementation with or without a GUI. Thus, waveform definition circuit 320, including its various embodiments discussed in this document, may be implemented as part of a GUI as specifically illustrated in this document by way of example, or otherwise implemented as part of a programming device such as programming device 302 including its various embodiments discussed in this document.

In various embodiments, GUI 310 includes any type of presentation device, such as interactive or non-interactive screens, and any type of user input devices that allow the user to edit the graphical representation of the accessed waveform, such as touchscreen, keyboard, keypad, touchpad, trackball, joystick, and mouse. In one embodiment, GUI 310 includes an interactive touchscreen and displays the graphical representation of the accessed waveform by visually indicating parameters defining the accessed waveform on the touchscreen. The touchscreen allows the user to modify one or more parameters of the visually indicated parameters, such as by dragging one or more segments of the accessed waveform.

In various embodiments, circuits of neurostimulation 100, including its various embodiments discussed in this document, may be implemented using a combination of hardware and software. For example, the circuit of GUI 110 including waveform definition circuit 320, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
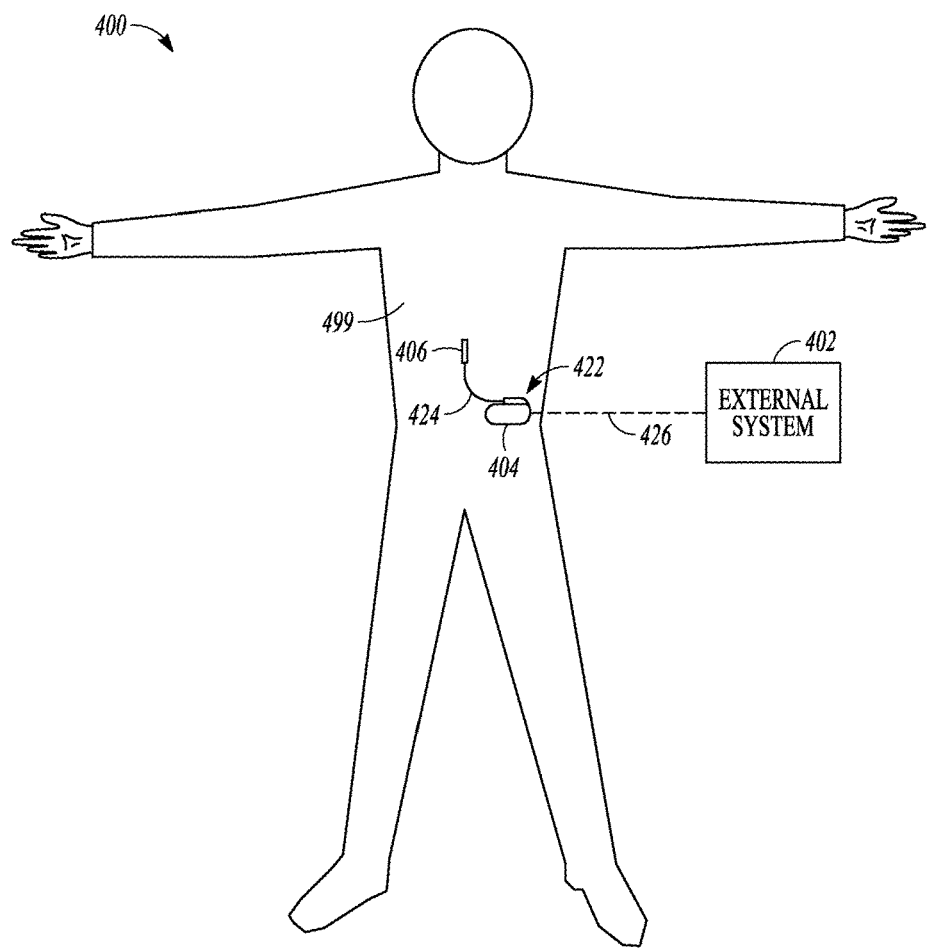
FIG. 4 illustrates an implantable neurostimulation system and portions of an environment in which the implantable neurostimulation system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in a patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

While an implantable neurostimulation system is discussed as a specific example, the present subject matter is not limited to implantable neurostimulation systems, and is not limited to either implantable systems or neurostimulation systems. In various embodiments, the definition of stimulation waveform including the insertion and/or adjustment of charge recovery phases as discussed in this document can be implemented in any neurostimulation system, such as an implantable neurostimulation system, a percutaneous neurostimulation system, or a transcutaneous neurostimulation system. In various embodiments, the definition of stimulation waveform including the insertion and/or adjustment of charge recovery phases as discussed in this document can also be implemented in any electrical stimulation systems that deliver electrical stimulation pulses with charge recovery phases to various target tissues or organs in patients.

Figure 5:
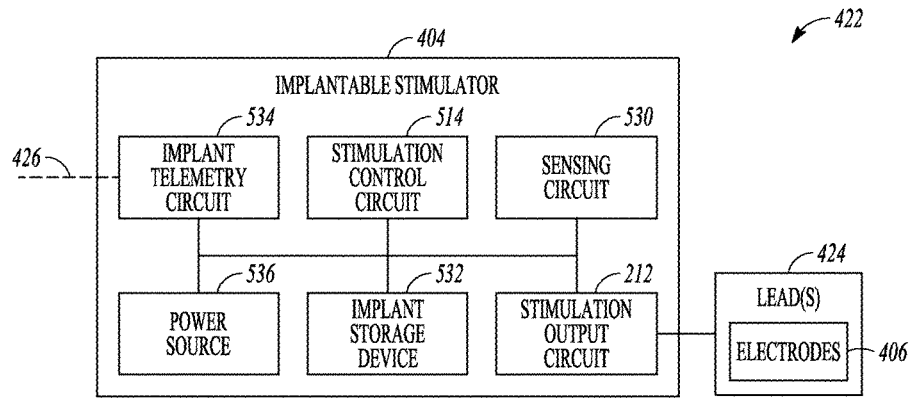
FIG. 5 illustrates an embodiment of an implantable stimulator and one or more leads of an implantable neurostimulation system, such as the implantable neurostimulation system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 406 through lead 424, and delivers each of the neurostimulation pulses through a set of electrodes selected from electrodes 406. Stimulation control circuit 514 represents an embodiment of stimulation control circuit 214 and controls the delivery of the neurostimulation pulses using the plurality of stimulation parameters specifying the pattern of neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
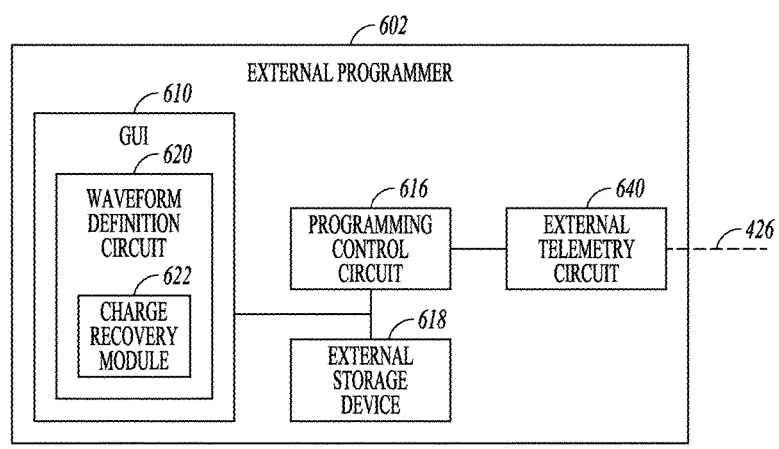
FIG. 6 illustrates an embodiment of an external programmer of an implantable neurostimulation system, such as the implantable neurostimulation system of FIG. 4.

FIG. 6 illustrates an embodiment of an external programmer 602 of an implantable neurostimulation system, such as external system 402 of system 400. External programmer 602 represents an embodiment of programming device 302, and includes an external telemetry circuit 640, an external storage device 618, a programming control circuit 616, and a GUI 610.

External telemetry circuit 640 provides external programmer 602 with wireless communication with another device such as implantable stimulator 404 via telemetry link 426, including transmitting the plurality of stimulation parameters to implantable stimulator 404. In one embodiment, external telemetry circuit 640 also transmits power to implantable stimulator 404 through an inductive couple.

External storage device 618 stores one or more stimulation waveforms, each stimulation waveform representing a pattern of neurostimulation pulses during a stimulation period. In various embodiments, each stimulation waveform can be selected for modification by the user and/or for use in programming a stimulation device such as implantable stimulator 404 to deliver a therapy. In this document, "the stimulation waveform" includes a stimulation waveform representing a pattern of neurostimulation pulses during a stimulation period, and may include a stimulation waveform selected from external storage device 618 or a new stimulation waveform to be added to the one or more stimulation waveforms stored in external storage device 618.

In various embodiments, the stimulation waveform is definable on a pulse-by-pulse basis, and external storage device 618 includes a pulse library that stores one or more individually definable pulse waveforms each defining a pulse type of one or more pulse types. External storage device 618 also stores one or more individually definable fields. Each pulse type of the one or more pulse types is associated with a field of the one or more individually definable fields. Each field of the one or more individually definable fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, based on the pattern of neurostimulation pulses. The pattern may be created and/or adjusted by the user using GUI 610 and stored in external storage device 618. In various embodiments, programming control circuit 616 checks values of the plurality of stimulation parameters against safety rules to limit these values within constraints of the safety rules. In one embodiment, the safety rules are heuristic rules.

GUI 610 represents an embodiment of GUI 310 and allows the user to define the pattern of neurostimulation pulses by creating and/or editing the stimulation waveform representing the pattern. GUI 610 includes a waveform definition circuit 620, which represents an embodiment of waveform definition circuit 320. Waveform definition circuit 620 allows for definition of the stimulation waveform representing a pattern of neurostimulation pulses during a stimulation period and includes a charge recovery module 622. Examples of defining a stimulation waveform using a GUI, such as GUI 610, are discussed in U.S. Provisional Patent Application No. 62/050,505, entitled "GRAPHICAL USER INTERFACE FOR PROGRAMMING NEUROSTIMULATION PULSE PATTERNS," filed on Sep. 15, 2014 and U.S. Provisional Patent Application No. 62/075,079, entitled "METHOD AND APPARATUS FOR PROGRAMMING COMPLEX NEURO STIMULATION PATTERNS," filed on Nov. 4, 2014, both assigned to Boston Scientific Neuromodulation Corporation, which are incorporated by reference in their entirety. In various embodiments, waveform definition circuit 620 with charge recovery module 622 allow for definition of the stimulation waveforms in ways identical or similar to these examples, but without requiring a charge recovery phase for each pulse in the pattern of neurostimulation pulses as discussed in these examples. In various embodiments, charge recovery module 622 receives the stimulation waveform with each neurostimulation pulse in the pattern of the neurostimulation pulses including a charge injection phase, receives a charge recovery scheme, identifies a need for recovering charges injected during the charge injection phases, and adjusts the received stimulation waveform by automatically inserting charge recovery phases into the received stimulation waveform based on the identified need for recovering the injected charges and the received charge recovery scheme.

In various embodiments, waveform definition circuit 620, including charge recovery module 622, provides a user with the capability of generating a complex stimulation waveform without initially considering the charge recover phases. Given a complex stimulation waveform with uncompleted charge recovery phases, the user may define a charge recovery scheme according to which a computerized device such as external programmer 602 can insert the charge recovery phases. For example, after a stimulation waveform is created with charge injection phases, the user can specify that the charge recovery phase should occur every 20 milliseconds±100 microseconds. Charge recovery module 622 then automatically insert the charge recovery phases into the stimulation waveform to meeting that criterion as well as other criteria that may be specified by the user or stored in external storage device 618. Use of a GUI is not necessary for automatic definition of the charge recovery phases. However, when GUI 610 is used, the user can enter and adjust the charge recovery scheme and make adjustment to the stimulation waveform in a more intuitive way. In various embodiments, charge recovery module 622 can monitor whether an acceptable level of charge balance can be achieved based on the stimulation waveform and the charge recovery scheme entered by the user, and warn the user when the acceptable level of charge balance cannot be achieved. The user may then adjust the charge recover scheme and/or the stimulation waveform to more completely recover the charges injected with the neurostimulation charges. In various embodiments, waveform definition circuit 620, including charge recovery module 622, reduces or removes the burden of considering charge recovery phases during the creation of a stimulation waveform, thereby allowing the user to focus on defining the charge injection phases that provide the desired pattern of evoked action potentials in the target tissue of the neurostimulation. Examples of charge injection and charge recovery pulses are discussed in U.S. Patent Application Publication No. 2014/0243924 A1. In various embodiments, after such charge injection pulses are defined, charge recovery module 620 completes the definition of the complete stimulation waveform by automatically inserting such charge recovery pulses.

In various embodiments, GUI 610 allows for export of a stimulation waveform of the one or more stimulation waveforms stored in external storage device 618 from external programmer 602. In various embodiments, GUI 610 allows for import of a stimulation waveform into external programmer 602 to be added to the one or more stimulation waveforms stored in external storage device 618. In various embodiments, GUI 610 allows for export of one or more pulse types and/or fields stored in external storage device 618 from external programmer 602. In various embodiments, GUI 610 allows for import of one or more pulse types and/or fields into external programmer 602 to be added to the one or more pulse types and/or fields stored in external storage device 618. Such imports and exports enable the user to share stimulation waveforms and/or their building blocks with other users in a community of users that use the same or similar neurostimulation systems to treat patients.

Figure 7:
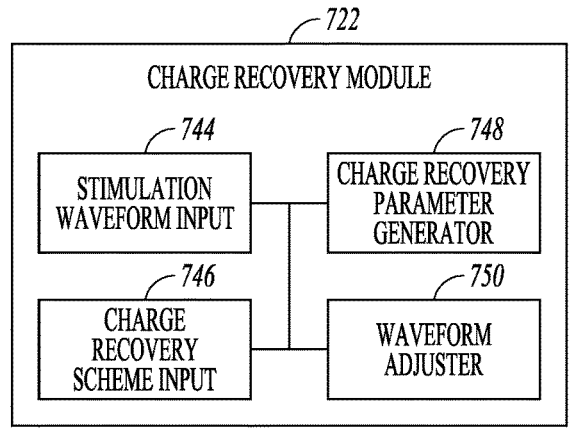
FIG. 7 illustrates an embodiment of a charge recovery module of the external programmer of FIG. 6.

FIG. 7 illustrates an embodiment of a charge recovery module 722, which represents an embodiment of charge recovery module 722. In the illustrated embodiment, charge recovery module 722 includes a stimulation waveform input 744, a charge recovery scheme input 746, a charge recovery parameter generator 748, and a waveform adjuster 750.

Stimulation waveform input 744 receives the stimulation waveform with each neurostimulation pulse in the pattern of the neurostimulation pulses including a charge injection phase. In one embodiment, the stimulation waveform may include only charge injection phases. In another embodiment, the stimulation waveform may include charge injection phases and charge recovery phases, but whether the charge recovery phases are properly placed in the stimulation waveform needs to be verified, and necessary or desirable modification may be made based on the outcome of the verification.

Charge recovery scheme input 746 receives the charge recovery scheme. In one embodiment, charge recovery scheme input 746 receives the charge recovery scheme from the user using the GUI. In various embodiments, charge recovery scheme input 746 may receive the charge recovery scheme in forms of selection, parameter value, answer to a question, and/or any expression that allows for definition of the charge recovery scheme.

In one embodiment, charge recovery scheme input 746 is configured to present a predefined charge recovery scheme and allow the user to define parameters for that scheme. For example, charge recovery scheme input 746 can display one or more parameters associated with the charge recovery scheme and receive a value for each parameter of the displayed one or more parameters. To allow the user to enter the value, charge recovery scheme input 746 can display a range and receive a value within the displayed range, or display a plurality of predefined values and receive a selection of a value from the displayed plurality of predefined values. Examples of such one or more parameters include current amplitude for the charge recovery phase, interphase interval (time interval between the end of a charge injection phase to the beginning of the subsequently adjacent charge recovery phase), and duration of the charge recovery phase. Charge recovery scheme input 746 can display one or more questions associated with the charge recovery scheme and receive an answer for each questions of the displayed one or more questions. To allow the user to enter the answer, charge recovery scheme input 746 can display a plurality of predefined answers and receive a selection of an answer from the displayed plurality of predefined answers. Example of the one or more questions include whether a charge recovery phase should be stopped or interrupted if the next charge injection phase is scheduled to start, whether the charge recovery phases for multiple charge injection phases are allowed to overlap (superimposed on each other), whether the charge recovery phases can be contiguous and whether active or passive charge recovery is to be performed.

In another embodiment, charge recovery scheme input 746 is configured to display a plurality of predefined charge recovery schemes and receive a selection of a charge recovery scheme from the displayed plurality of predefined charge recovery schemes. Examples of the predefined charge recovery schemes include charge recovery phases each occurring with a specified maximum time interval after each of the charge injection phases and periodic charge recovery phases at specified frequency, applied as needed, and non-overlapping with charge injection phases. Charge recovery scheme input 746 can further display one or more parameters based on the selection of the charge recovery scheme and receive a value for each parameter of the displayed one or more parameters. To allow the user to enter the value, charge recovery scheme input 746 can display a range and receive a value within the displayed range, or display a plurality of predefined values and receive a selection of a value from the displayed plurality of predefined values. Charge recovery scheme input 746 can also further display one or more questions based on the selection of the charge recovery scheme and receive an answer for each questions of the displayed one or more questions, To allow the user to enter the answer, charge recovery scheme input 746 can display a plurality of predefined answers and receive a selection of an answer from the displayed plurality of predefined answers.

Charge recovery parameter generator 748 generates a plurality of charge recovery parameters based on the received charge recovery scheme. In one embodiment, charge recovery parameter generator 748 generates the plurality of charge recovery parameters based on the received charge recovery scheme and predetermined default values. The predetermined default values can include one or more limiting values for one or more charge recovery parameters of the plurality of charge recovery parameters. Examples of such one or more limiting values include minimum current amplitude of the charge recovery phases, maximum current amplitude of the charge recovery phases, maximum time allowed for completing charge recovery, and minimum interphase interval maximum interphase interval.

Waveform adjuster 750 identifies a need for recovering charges injected during the charge injection phases and adjusts the received stimulation waveform by automatically inserting charge recovery phases into the received stimulation waveform based on the identified need for recovering the injected charges and the plurality of charge recovery parameters. In various embodiments, the need for recovering charges injected during the charge injection phases is specific for neurostimulation pulses delivered using each unique set of electrodes, and the charge recovery phases are inserted for charge balance associated with that set of electrodes.

In various embodiments, waveform adjuster 750 produces a warning signal in response to the adjusted stimulation waveform not having an acceptable level of charge balance after the charge recovery phases are inserted. The warning signal may include a message indicating that the charge balance cannot be achieved based on the received stimulation waveform and the received charge recovery scheme (or the plurality of charge recovery parameters). In response, the user is allowed to modify the charge recovery scheme and/or the adjusted stimulation waveform.

In various embodiments in which a GUI is employed, waveform adjuster 750 displays the adjusted stimulation waveform (with the inserted charge recovery phases), and allows the user to adjust the displayed stimulation waveform using the GUI. In various embodiments, waveform adjuster 750 can be configured to allow the user to graphically edit the stimulation waveform (including editing both the charge recovery pulses and the charge injection pulses), graphically edit only the charge recovery phases, or graphically editing only the charge injection phases.

Figure 8:
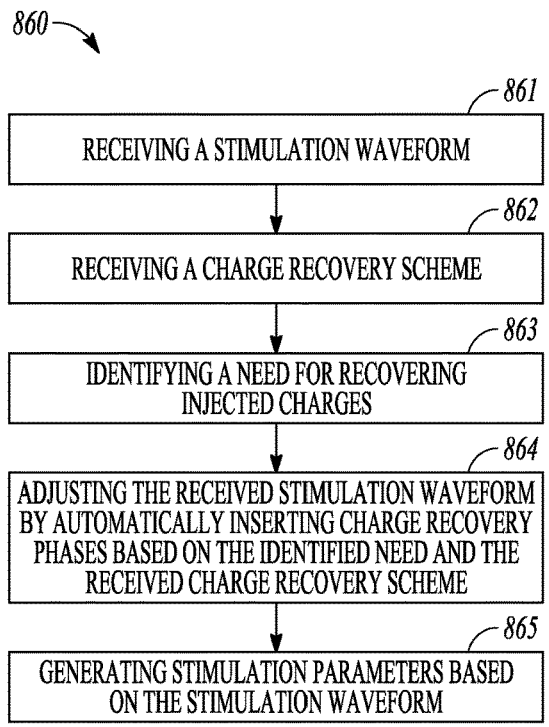
FIG. 8 illustrates an embodiment of a method for automatically inserting charge recovery phases into a stimulation waveform.

FIG. 8 illustrates an embodiment of a method 860 for automatically inserting charge recovery phases into a stimulation waveform. In one embodiment, a neurostimulation system such as system 100 or 400, including the various embodiments of their component as discussed in this document, is configured to perform method 860. In various embodiments, method 860 allows for controlling neurostimulation by a user such as a physician or other caregiver who treats a patient using the neurostimulation system.

At 861, a stimulation waveform representing a pattern of neurostimulation pulses during a stimulation period is received. Each pulse in the pattern of the neurostimulation pulses includes a charge injection phase. At 862, a charge recovery scheme is received from the user. At 863, optionally a need for recovering charges injected during the charge injection phases is identified. This step may not be necessary if the received stimulaton waveform is known to be not charge-balanced. At 864, the received stimulation waveform is adjusted by automatically inserting charge recovery phases into the received stimulation waveform based on the identified need for recovering the injected charges and the received charge recovery scheme using a processing circuit of the programming device. At 865, a plurality of stimulation parameters is generated based on the stimulation waveform. The plurality of stimulation parameters allows for delivery of the neurostimulation from a stimulation device to be controlled according to the stimulation waveform.

Figure 9:
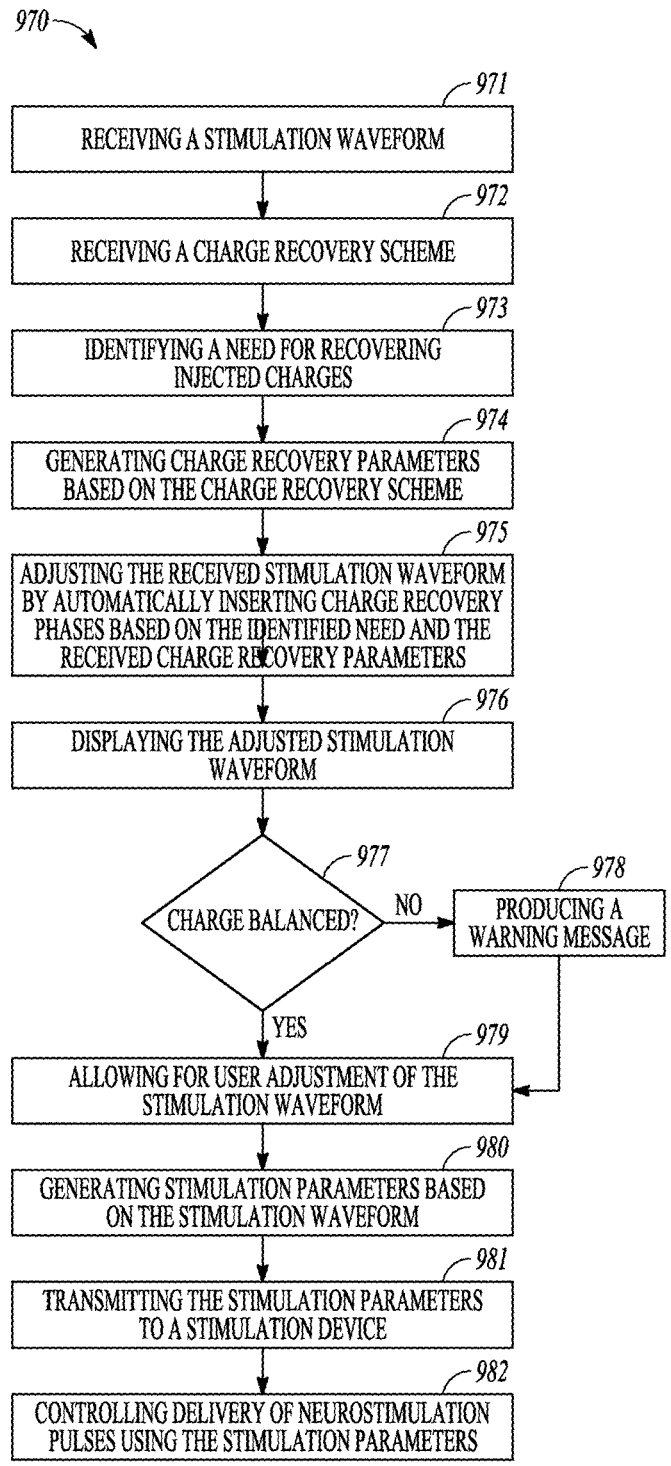
FIG. 9 illustrates another embodiment of a method for automatically inserting charge recovery phases into a stimulation waveform.

FIG. 9 illustrates an embodiment of a method 970 for automatically inserting charge recovery phases into a stimulation waveform. In one embodiment, a neurostimulation system such as system 100 or 400, including the various embodiments of their components as discussed in this document, is configured to perform method 970. In various embodiments, method 970 allows for controlling neurostimulation by a user such as a physician or other caregiver who treats a patient using the neurostimulation system.

At 971, a stimulation waveform is received. The stimulation waveform represents a pattern of neurostimulation pulses during a stimulation period. Each neurostimulation pulse in the pattern of the neurostimulation pulses includes a charge injection phase. In various embodiments, the stimulation waveform may include only charge injection phases or both charge injection phases and charge recovery phases. When the stimulation waveform includes both charge injection phases and charge recovery phases, method 970 can be performed to verify that the charge recovery phases are properly placed in the stimulation waveform and modify the charge recovery phases when necessary or desired.

At 972, a charge recovery scheme is received from the user. In one embodiment, the charge recovery scheme is received using a GUI of a programming device. In one embodiment, one or more parameters associated with the charge recovery scheme are displayed if needed, and a value for each parameter of the displayed one or more parameters is received. In one embodiment, one or more questions associated with the charge recovery scheme are displayed if needed, and an answer for each questions of the displayed one or more questions is received. In one embodiment, a plurality of predefined charge recovery schemes is displayed, and a selection of a charge recovery scheme from the displayed plurality of predefined charge recovery schemes is received. If one or more parameters need to be specified, and/or one or more questions need to be answered, for the selected charge recovery scheme, the one or more parameters are displayed and a value for each parameter of the displayed one or more parameters is received, and/or the one or more questions are displayed and an answer for each questions of the displayed one or more questions is received.

At 973, a need for recovering charges injected during the charge injection phases is identified. This can include identifying the charge injection phases in the received stimulation waveform and determining whether the stimulation waveform has included charge recovery phases to properly recover the injected charges. In various embodiments, step 973 may be optional depending on whether it is known that the received stimulation waveform is not charge-balanced. In various embodiments, when the received stimulation waveform is known to include both charge injection phases and charge recovery phases, step 973 can be performed to verify that the charge injection phases provide a satisfactory level of charge balance and adjust the stimulation waveform if needed.

At 974, a plurality of charge recovery parameters is generated based on the received charge recovery scheme. The received charge recovery scheme may include the value for each parameter of the displayed one or more parameters and/or the answer for each questions of the displayed one or more questions. In various embodiments, the plurality of charge recovery parameters is generated based on the received charge recovery scheme and one or more predetermined values for one or more parameters of the plurality of charge recovery parameters. Examples of such one or more predetermined values include one or more limits each being a maximum or minimum value determined to ensure effective charge recovery.

At 975, the received stimulation waveform is adjusted by automatically inserting charge recovery phases into the received stimulation waveform based on the plurality of charge recovery parameter using a processing circuit, such as a processing circuit of a programming device in the neurostimulation system. In various embodiments, the charge injection phases in the received stimulation waveform are identified for each common set of electrodes, and charge recovery phases are inserted to balance the charges injected through the each common set of electrodes, based on the plurality of charge recovery parameters.

At 976, the adjusted stimulation waveform with the automatically inserted charge recovery phases is displayed. At 977, whether the adjusted stimulation waveform has an acceptable level of charge balance is determined. If the acceptable level of charge balance is not achieved, a warning message is produced at 978 to warn the user. The warning message indicates that the charge balance cannot be achieved based on the received stimulation waveform and the received charge recovery scheme (or the plurality of charge recovery parameters).

At 979, regardless of whether the acceptable level of charge balance is achieved, the user is allowed to adjust the stimulation waveform. This may include allowing the user to manually modifying the stimulation waveform using the GUI. In various embodiments, the user may be allowed to graphically edit the entire stimulation waveform, graphically edit only the charge recovery phases that are inserted into the received stimulation waveform, or graphically edit only the charge injection phases (and repeat the automatic insertion of the charge recovery phases).

At 980, a plurality of stimulation parameters is generated based on the stimulation waveform. The plurality of stimulation parameters allows for delivery of neurostimulation from a stimulation device to be controlled according to the stimulation waveform. In one embodiment, the stimulation device is an implantable neurostimulator. At 981, the plurality of stimulation parameters is transmitted to the stimulation device. At 982, delivery of the neurostimulation pulses from the stimulation device is controlled using the plurality of stimulation parameters.

Figure 10:
FIG. 10 illustrates an example of a stimulation waveform without charge recovery phases.

FIG. 10 illustrates an example of a stimulation waveform without charge recovery phases. It may represent a segment of the "received stimulation waveform" (which as illustrated includes only charge injection phases) as discussed above in this document. For illustration purposes only, the segment of the received stimulation waveform includes six charge injection phases 1090A-F of six neurostimulation pulses. In the illustrated example, charge injection phases 1090A-D are considered to be too close to each other to allow insertion of a charge recovery phase between any two of them, while charge injection phases 1090E-F are each followed by a non-stimulation time interval long enough to allow insertion of a charge recovery phase for immediate balancing of the charge injected with each pulse.

Figure 11:
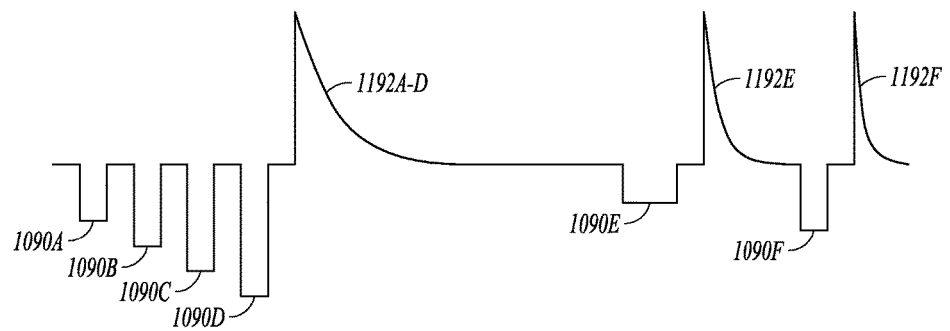
FIG. 11 illustrates an example of the stimulation waveform of FIG. 10 with charge recovery phases inserted.
Figure 12:
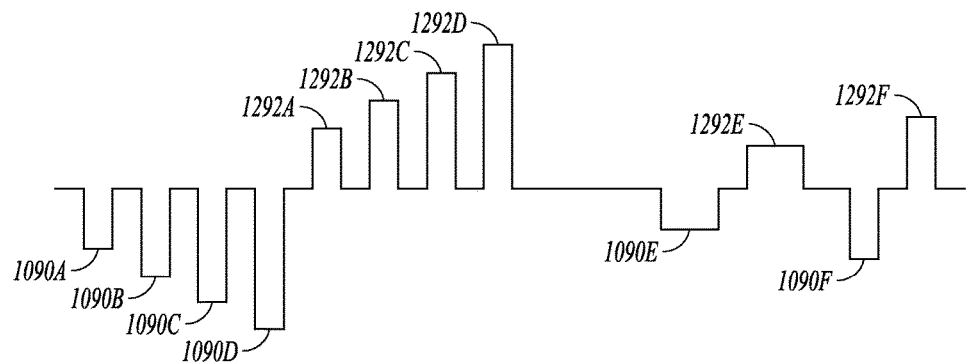
FIG. 12 illustrates another example of the stimulation waveform of FIG. 10 with charge recovery phases inserted.
Figure 13:
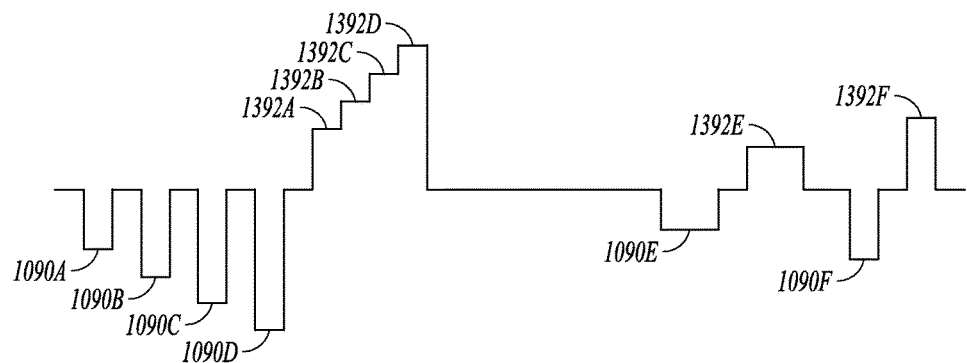
FIG. 13 illustrates another example of the stimulation waveform of FIG. 10 with charge recovery phases inserted.

FIGS. 11-13 each illustrates an example of the stimulation waveform of FIG. 10 with charge recovery phases inserted. The stimulation waveform in each of FIGS. 11-13 may represent a different example for the segment of the received stimulation waveform adjusted by automatically inserting charge recovery phases based on a different charge recovery scheme defined by the user. FIG. 11 illustrates an example of the stimulation waveform adjusted by inserting a passive charge recovery phase 1192A-D that balances the sum of the charges injected during charge injection phases 1090A-D, a passive charge recovery phase 1192E that balances the charges injected during charge injection phase 1090E, and a passive charge recovery phase 1192F that balances the charges injected during charge injection phase 1090F. FIG. 12 illustrates an example of the stimulation waveform adjusted by inserting noncontiguous active charge recovery phases 1292A-D each balancing the charges injected during one of charge injection phases 1090A-D, an active charge recovery phase 1292E that balances the charges injected during charge injection phase 1090E, and an active charge recovery phase 1292F that balances the charges injected during charge injection phase 1090F. FIG. 13 illustrates an example of the stimulation waveform adjusted by inserting contiguous active charge recovery phases 1392A-D each balancing the charges injected during one of charge injection phases 1090A-D, an active charge recovery phase 1392E that balances the charges injected during charge injection phase 1090E, and an active charge recovery phase 1392F that balances the charges injected during charge injection phase 1090F.

The waveforms in FIGS. 10-13 are shown by way of example, and not by way of limitation, to illustrate the "received stimulation waveform" and the "adjusted stimulation waveform" as discussed above in this document. In various embodiments, the present subject matter applies to any stimulation waveform that needs to be charge-balanced. Additional examples of such stimulation waveforms are discussed in U.S. Patent Application Publication No. 2014/0243924 A1.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for neurostimulation, comprising:
   determining a stimulation waveform representing a pattern of neurostimulation pulses each including a charge injection phase;
   generating charge recovery parameters based on a charge recovery scheme and one or more predetermined values of each parameter of one or more of the charge recovery parameters;
   adjusting the determined stimulation waveform by automatically inserting charge recovery phases into the determined stimulation waveform to recover charges injected during the charge injection phases using the charge recovery parameters; and
   programming a stimulation device for delivering the neurostimulation pulses according to the adjusted stimulation waveform.

2. The method of claim 1, wherein programming the stimulation device comprises:
   generating a plurality of stimulation parameters based on the adjusted stimulation waveform; and
   transmitting the plurality of stimulation parameters to an implantable stimulator.

3. The method of claim 1, further comprising storing one or more limits as the one or more predetermined values of each parameter of the one or more of the charge recovery parameters, the one or more limits each being a maximum or minimum value determined to ensure effective charge recovery.

4. The method of claim 1, further comprising:
   displaying the stimulation waveform using a graphical user interface (GUI); and
   allowing a user to adjust the displayed stimulation waveform.

5. The method of claim 4, wherein allowing the user to adjust the displayed stimulation waveform comprises allowing the user to graphically edit the charge recovery phases in the displayed stimulation waveform using the GUI.

6. The method of claim 4, wherein allowing the user to adjust the displayed stimulation waveform comprises allowing the user to graphically edit the charge injection phases in the displayed stimulation waveform using the GUI.

7. The method of claim 1, further comprising receiving the charge recovery scheme from a user using a user interface.

8. The method of claim 7, wherein receiving the charge recovery scheme from the user comprises:
   presenting a plurality of charge recovery schemes using the user interface; and
   allowing the user to select the charge recovery scheme from the presented plurality of predefined charge recovery schemes using the user interface.

9. The method of claim 8, further comprising indicating to the user that an acceptable level of charge balance is not achieved based on the determined stimulation waveform and the selected charge recovery scheme.

10. The method of claim 1, further comprising at least one of:
    displaying one or more parameters associated with the charge recovery scheme and receiving a value for each parameter of the displayed one or more parameters, or
    displaying one or more questions associated with the charge recovery scheme and receiving an answer for each questions of the displayed one or more questions.

11. A neurostimulation system, comprising:
    a programming control circuit configured to generate a plurality of stimulation parameters controlling delivery of the neurostimulation pulses according to a stimulation waveform representing a pattern of neurostimulation pulses each including a charge injection phase; and a waveform definition circuit coupled to the programming control circuit and configured to adjust the stimulation waveform, the waveform definition circuit including:
- a charge recovery parameter generator configured to generate a plurality of charge recovery parameters based on a charge recovery scheme and one or more predetermined values of each parameter of one or more of the charge recovery parameters; and
- a waveform adjuster configured to determine a stimulation waveform and to adjust the determined stimulation waveform by automatically inserting charge recovery phases into the stimulation waveform using the plurality of charge recovery parameters.

12. The system of claim 11, comprising a programmer including the programming control circuit and the waveform definition circuit.

13. The system of claim 12, further comprising an implantable stimulation device including a stimulation output circuit configured to deliver the neurostimulation pulses and a stimulation control circuit configured to control the delivery of the neurostimulation pulses using the plurality of stimulation parameters, and wherein the programmer is an external programmer configured to be communicatively coupled to the implantable stimulation device.

14. The system of claim 11, wherein the charge recovery parameter generator is configured to generate the plurality of charge recovery parameters based on the charge recovery scheme and one or more predetermined maximum or minimum values for one or more charge recovery parameters of the plurality of charge recovery parameters to ensure effective charge recovery.

15. The system of claim 11, comprising a user interface including a charge recovery scheme input configured to receive user input associated with the charge recovery scheme.

16. The system of claim 15, wherein the charge recovery scheme input is configured to display one or more parameters associated with the received charge recovery scheme and receive a value for each parameter of the displayed one or more parameters.

17. The system of claim 15, wherein the charge recovery scheme input configured to display one or more questions associated with the received charge recovery scheme and receive an answer for each questions of the displayed one or more questions.

18. The system of claim 15, wherein the charge recovery scheme input is configured to display a plurality of charge recovery schemes and receive the charge recovery scheme by receiving a selection from the displayed plurality of charge recovery schemes.

19. The system of claim 18, wherein the waveform adjuster is configured to produce a warning message in response to the adjusted stimulation waveform not having an acceptable level of charge balance.

20. A non-transitory computer-readable storage medium including instructions, which when executed by a system, cause the system to perform a method comprising:
- determining a stimulation waveform representing a pattern of neurostimulation pulses each including a charge injection phase;
- generating charge recovery parameters based on a charge recovery scheme and one or more predetermined values of each parameter of one or more of the charge recovery parameters;
- adjusting the determined stimulation waveform by automatically inserting charge recovery phases into the determined stimulation waveform to recover charges injected during the charge injection phases using the charge recovery parameters; and
- programming a stimulation device for delivering the neurostimulation pulses according to the adjusted stimulation waveform.

* * * * *